United States Patent
Kuchroo et al.

(10) Patent No.: US 9,732,320 B2
(45) Date of Patent: Aug. 15, 2017

(54) SELECTIVE DIFFERENTIATION, IDENTIFICATION, AND MODULATION OF HUMAN TH17 CELLS

(71) Applicant: THE BRIGHAM AND WOMEN'S HOSPITAL, INC., Boston, MA (US)

(72) Inventors: Vijay K. Kuchroo, Newton, MA (US); David E. Anderson, Boston, MA (US); Estelle Bettelli, Newcastle, WA (US); David Hafler, Newton, MA (US); Mohammed Oukka, Newcastle, WA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/517,116

(22) Filed: Oct. 17, 2014

(65) Prior Publication Data

US 2015/0050732 A1 Feb. 19, 2015
US 2017/0159016 A9 Jun. 8, 2017

Related U.S. Application Data

(62) Division of application No. 12/863,373, filed as application No. PCT/US2009/031477 on Jan. 21, 2009, now abandoned.

(60) Provisional application No. 61/031,824, filed on Feb. 27, 2008, provisional application No. 61/006,541, filed on Jan. 18, 2008.

(51) Int. Cl.
*C12N 5/00* (2006.01)
*C12N 5/02* (2006.01)
*C12N 5/0783* (2010.01)

(52) U.S. Cl.
CPC ................. *C12N 5/0636* (2013.01)

(58) Field of Classification Search
None
See application file for complete search history.

(56) References Cited

U.S. PATENT DOCUMENTS

| 7,622,443 B2 | 11/2009 | Anderson et al. |
| 8,178,104 B2 | 5/2012 | Ruoslahti et al. |
| 8,288,357 B2 | 10/2012 | Kim et al. |
| 9,255,272 B2 * | 2/2016 | Kim ............. C07K 16/28 |
| 2011/0008795 A1 * | 1/2011 | Ikeda ............. C12Q 1/6881 435/6.16 |
| 2011/0136113 A1 | 6/2011 | Uga et al. |

FOREIGN PATENT DOCUMENTS

| WO | 2005107725 A1 | 11/2005 |
| WO | 2006007468 A2 | 1/2006 |

OTHER PUBLICATIONS

Zhang et al. (J of Immunol. 2011, v.186 Supl.1.*
Kihara et at(Biochem. And Blophys. Research. Comm., 2010, v.394, pp. 673-678).*
Ivanov et al., Semin. Immunol., 19(6):409-417 (2007). "Transcriptional regulation of TH17 cell differentiation."
Nurieva et al., Nature, 448:480-484 (2007). "Essential autocrine regulation by IL-21 in the generation of inflammatory T cells."
Veldhoen et al., Immunity, 24(2):179-189 (2006). "TGFbeta in the context of an inflammatory cytokine milieu supports de novo differentitation of IL-17-producing T cells."
Yang et al., Nature, 454:350-352 (2008). "IL-21 and TGFbeta are required for differentiation of human Th17 cells."
Database OMIM [Online] 2009, "Podoplanin; PDPN", XP002644964, retrieved from NCBI, Database accession No. 608863.
Suzuki et al., "Induction of podoplanin by transforming growth factor-beta in human fibrosarcoma", FEBS Letters, 582 (2): 341-345 (2008).
Wicki et al., "The potential role of podoplanin in tunour invasion", British Journal of Cancer, 96(1): 1-5 (2007).

* cited by examiner

*Primary Examiner* — Michail Belyavskyi
(74) *Attorney, Agent, or Firm* — Nixon Peabody LLP; David S. Resnick; Mark J. FitzGerald

(57) ABSTRACT

The embodiments provide for the modulation of both the differentiation and activity of human $T_H17$ cells. More specifically, human $T_H17$ cell differentiation can modulated by TGF-β and IL-21, and their agonists and antagonists. Function of $T_H17$ cells can be modulated by, for example, BLT1 or podoplanin, and their agonists and antagonists. Additionally, the embodiments provide for the identification of $T_H17$ cells. More specifically, human $T_H17$ cells specifically upregulate BLT1 and podoplanin.

1 Claim, 11 Drawing Sheets

SELECTIVE DIFFERENTIATION, IDENTIFICATION, AND MODULATION OF HUMAN TH17 CELLS

RELATED PATENT APPLICATIONS

This Application is a divisional application of U.S. application Ser. No. 12/863,373 filed on Jul. 16, 2010 (now abandoned), which is a 35 U.S.C. §371 National Phase Entry Application of International Application No. PCT/US09/31477 filed Jan. 21, 2009, which designates the U.S., and which claims the benefit of priority from U.S. Patent application Ser. No. 61/006,541, filed Jan. 18, 2008, and Ser. No. 61/031,824, filed Feb. 27, 2008.

FEDERAL FUNDING LEGEND

The invention was made, in part, with government support under grants No. P01 NS038037, No. NS045937 and No. 30843, awarded by the National Institutes of Health. The U.S. government has certain rights in the invention.

BACKGROUND

Autoimmune diseases, more than eighty of which have been identified, cause significant morbidity and disability and are notoriously difficult to diagnose. As many as twenty-four million Americans suffer from autoimmune disease, and treatment costs exceed $100 billion annually.

Recently, a new population of effector cells, T$_H$17 cells, has been identified and implicated in various immune-related conditions. The discovery of these cells has had a major impact on the understanding of immune processes not readily explained by the T$_H$1/T$_H$2 paradigm. Importantly, T$_H$17 cells have been associated with the pathogenesis of human autoimmune diseases including multiple sclerosis, rheumatoid arthritis, inflammatory bowel disease, and psoriasis.

Further understanding of the differentiation, expansion, and function of T$_H$17 cells in human cells, in association with rodent models, and a method for specifically identifying T$_H$17 cells remain important goals in the exploration of autoimmune and other human diseases.

SUMMARY

The present embodiments provide for the differentiation of human T$_H$17 cells. More specifically, the present invention refines and extends the understanding of the regulation of IL-17A secretion from human CD4$^+$ T cells, and defines the conditions required for human T$_H$17 cell differentiation.

In a one embodiment, the invention provides for a method of increasing the differentiation of human T$_H$17 cells from a population of human naïve CD4$^+$ T cells by contacting the T cells with TGF-β and IL-21 in amounts sufficient to increase human T$_H$17 cell differentiation.

Another embodiment provides for a method of regulating the level of expression of IL-17 from human naïve CD4$^+$ T cells by contacting said cells with TGF-β and IL-21 in amounts sufficient to increase IL-17 expression.

Yet another embodiment provides a method for increasing T$_H$17 cell activity and/or T$_H$17 cell number by (optionally) identifying a cell (a T cell), or a cell population, where T$_H$17 differentiation is desired, and contacting said cell or cell population with a TGF-β agonist and a IL-21 agonist in an amount sufficient to increase differentiation into T$_H$17 cells, thereby increasing T$_H$17 cell activity and/or cell number.

The present invention also provide for a method for inhibiting precursor T cell or T cell population differentiation into a T$_H$17 cell or T$_H$17 cell population by contacting the T cell or T cell population with an antagonist of a TGF-β and IL-21, or a TGF-βR and IL-21R, in amounts sufficient to inhibit T$_H$17 cell differentiation.

An alternative embodiment provides a method for modulating one or more of: IL-17 activity, expression, secretion, or processing, in a T cell or a T$_H$17 cell, or a cell population thereof, is provided by (optionally) identifying a cell in which modulation (increase or reduction) of the activity or level of IL-17 is desired; and contacting said cell or cell population with an amount of TGF-β/IL-21 modulators, e.g., TGF-β/IL-21 agonists or antagonists, sufficient to modulate the activity or level of IL-17 in said cell or cell population.

For example, the migration activity of T$_H$17 cells can be inhibited by U75-302, an antagonist of the T$_H$17-specific leukotriene B4. Similarly, the migration activity of T$_H$17 cells can be inhibited by podoplanin.

The present invention also provides for compositions, methods, and kits for identifying T$_H$17 cells, and for diagnosing and/or monitoring T$_H$17-associated autoimmune diseases. More specifically, the present invention identifies surface molecules specifically up-regulated in T$_H$17 cells. In an aspect of the invention, the molecule is the receptor for leukotreine B4 (LTBR4, also called BLT1). In another aspect, the molecule is podoplanin.

The present invention also relates to the use of TGF-β and IL-21 or agonists thereof for increasing the differentiation of human T$_H$17 cells from a population of naïve CD4+ T cells.

The present invention also relates to the use of antagonists of TGF-β and IL-21 to inhibit the differentiation of a T cell or T cell population into a T$_H$17 cell or T$_H$17 cell population.

The present invention also relates to the use of TGF-β and IL-21 or agonists thereof to increase the expression, activity, secretion or processing of IL-17 in a T cell or T cell population.

The present invention also relates to the use of antagonists of TGF-β and IL-21 to decrease the expression, activity, secretion or processing of IL-17 in a T cell or T cell population.

The present invention also relates to the use of an antagonist of TGF-β and an antagonist of IL-21 in the preparation of a medicament for the treatment of a disorder involving or mediated by T$_H$17 cell activity.

DESCRIPTION OF THE DRAWINGS

FIG. 1A shows CD4$^+$ T cells obtained from the peripheral blood of healthy subjects, sorted into populations enriched for naïve (CD4$^+$ CD25$^-$ CD62L$^+$ CD45RA$^{hi}$) or central memory (T$_{CM}$) (CD4$^+$ CD25$^-$ CD62L$^+$ CD45RA$^-$) T helper cells.

FIG. 1B shows sorted T cell populations that were stimulated for seven days in the presence of the indicated cytokines, at which point supernatants were collected and assessed for IFN-γ and IL-17A by ELISA. Error bars represent the standard deviation among three independent experiments using T cells from three unrelated subjects. Induction of IL-17A secretion by a combination of TGF-β and IL-21 is highly significant (p<0.01).

FIG. 1C shows naïve CD4$^+$ T cells stimulated in the presence or absence of TGF-β and IL-21 for seven days, at which point cells were washed, stimulated for five hours with PMA/ionomycin, and stained for intracellular expression of IL-17 and IFN-γ. Comparable results have been obtained in five unrelated donors.

FIG. 2A shows naïve CD4$^+$ T cells obtained from the peripheral blood of healthy subjects stimulated for seven days in the presence of the indicated cytokines, at which point RNA was collected and levels of RORC2, Tbet, GATA-3, IL-23R, and FoxP3 were measured by quantitative RT-PCR. The mean fold-induction (relative to T cells stimulated in the absence of exogenous cytokines) and standard error among three independent experiments using T cells from three unrelated subjects are represented.

FIG. 2B shows a mean fold-induction and standard error of IL-21 and IL-22 for three independent experiments.

FIG. 2C shows CD4$^+$ T cells obtained from cord blood sorted into a population enriched for naïve (CD4$^+$ CD25$^-$ CD62L$^+$ CD45RA$^{hi}$) T helper cells. Sorted T cells were stimulated for seven days in the presence of the indicated cytokines, at which point RNA was collected and levels of IL-17A and RORC2 were measured by quantitative RT-PCR. Mean expression and standard error are reported based on three independent experiments using cord blood from three distinct donors.

FIG. 2D reflects intracytoplasmic staining of IL-17 and IFN-γ from cord blood naive T cells after seven days of differentiation. Similar results were seen in another independent assay.

DETAILED DESCRIPTION

Figure 1A:
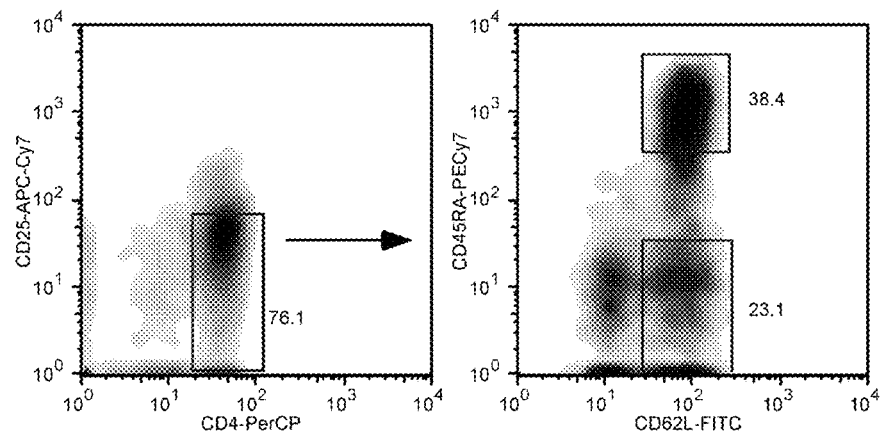
FIGS. 1A to 1C present data showing that TGF-β and IL-21 promote T$_H$17 differentiation from naïve CD4$^+$ T cells.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

CD4+ T helper cells (TH cells) of the adaptive immunity system have evolved to protect host against specific pathogens. TH cells have been divided into three subsets depending on both the cytokines that they produce and the effector functions that they accomplish. These TH cell subsets are designated TH1, TH2, and TH17 cells. Recently, TH17 cells have emerged as potent inducers of inflammation and autoimmune diseases. The mechanisms used by TH17 cells to accomplish their pathogenic functions remain elusive, driving the need for further understanding into the differentiation, characterization, and function of human TH17 cells.

The present invention defines the conditions required for human TH17 cell differentiation, and compositions and methods useful in modulating human TH17 cell differentiation and functionality.

The recent discovery of CD4+ T cells characterized by secretion of IL-17 (TH17 cells) and the regulatory, FoxP3+ CD4 T cell (nTREG) have had a major impact on the understanding of immune processes that are not readily explained by the traditional TH1/TH2 paradigm. Kikly et al., 18 Curr. Opin. Immunol. 670-75 (2006); Wilson et al., 8 Nature Immuno. 950-57 (2007). Recent work demonstrated that TGF-β and IL-6 are responsible for the differentiation of naïve murine T cells into TH17 cells, and it has been proposed that IL-23 may play a critical role in stabilization of the TH17 phenotype. Bettelli et al., 441 Nature 235-58 (2006); Mangan et al., 441 Nature 231-34 (2006); Veldhoen et al., 24 Immunity 179-89 (2006). It has also been discovered that a second pathway in which a combination of TGF-β and IL-21 is capable of inducing differentiation of murine TH17 cells in the absence of IL-6. Korn et al., 448 Nature 484-87 (2007); Nurieva et al., 448 Nature 480-83 (2007); Zhou et al., 8 Nature Immunol. 967-74 (2007).

TGF-β and IL-6 are not, however, capable of differentiating human TH17 cells. Wilson et al., 2007; Acosta-Rodriguez et al, 8 Nature Immunol. 942-49 (2007). It has been suggested that TGF-β may, in fact, suppress the generation of human TH17 cells. Evans et al., 104 P.N.A.S. 17034-39 (2007). Instead, it has recently been shown that the cytokines IL-1β, IL-6, and IL-23 are capable of driving IL-17 secretion in short-term CD4+ T cell lines isolated from human peripheral blood (Laurence & Shea, 8 Nature Immunol. 903-05 (2007)), though the factors required for differentiation of naïve human CD4 to TH17 cells remained unknown until the present invention. The present invention provides that although IL-1β and IL-6 induce IL-17A secretion from human central memory CD4+ T cells, TGF-β and IL-21 uniquely promote the differentiation of human naïve CD4+ T cells into TH17 cells, accompanied by expression of RORC2. The present invention will now facilitate the investigation of the role played by the population of TH17 cells in human inflammatory disease.

Figure 1B:
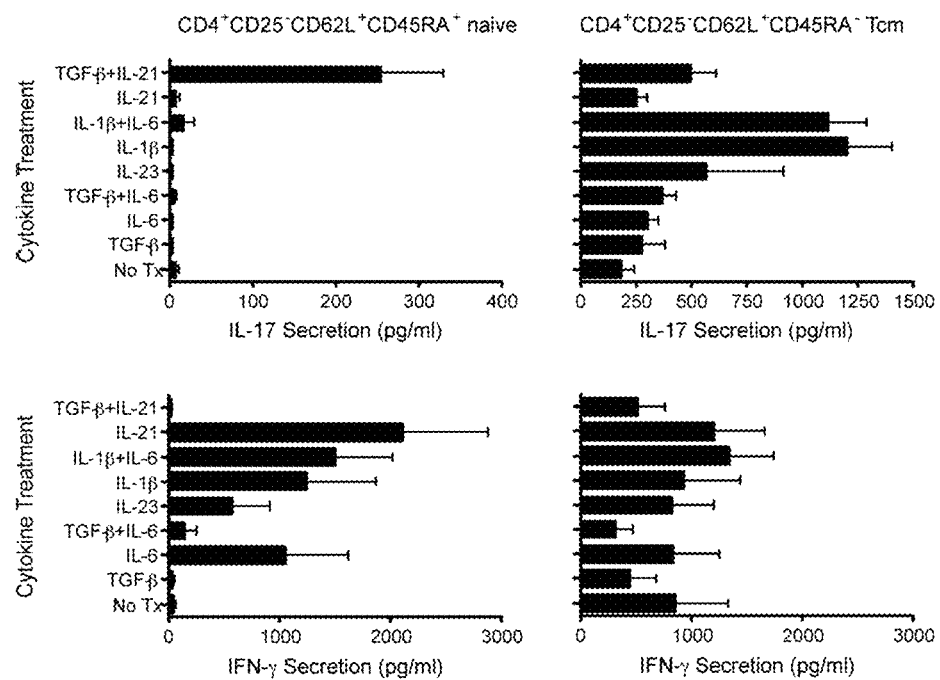

Better understanding of the regulation of IL-17A secretion from human CD4+ T cells required a strategy that would allow the evaluation of the effects of various cytokine combinations on expansion of IL-17-expressing cells from memory T cells, versus differentiation of naïve CD4 lymphocytes into TH17 cells. Specifically, high-speed flow cytometry was used to sort these two distinct populations of CD4+ T cells from the peripheral blood of healthy subjects: CD4+ CD25− CD62L+ CD45RA$^{hi}$ cells highly enriched for naïve T cells and CD4+ CD25− CD62L+ CD45RA− cells enriched for central memory T cells (TCM) (FIG. 1A). The cells enriched for a naïve phenotype were uniformly positive for CCR7 expression. These two T cell populations were then stimulated with plate-bound anti-CD3 and soluble anti-CD28 monoclonal antibodies for seven days in serum-free medium containing different combinations of cytokines implicated in CD4+ T cell differentiation. As previously reported, the cytokine interleukin-1β induced the greatest amount of IL-17A secretion from TCM (FIG. 1B). The addition of IL-6 alone had little effect on induction of IL-17A, and when added with IL-1β had no additive or synergistic effect on IL-17A production. Addition of IL-23 was also able to modestly enhance IL-17A secretion from TCM. IL-1β either alone or together with IL-6 failed, however, to induce IL-17A secretion from naïve CD4+ T cells.

Figure 1C:
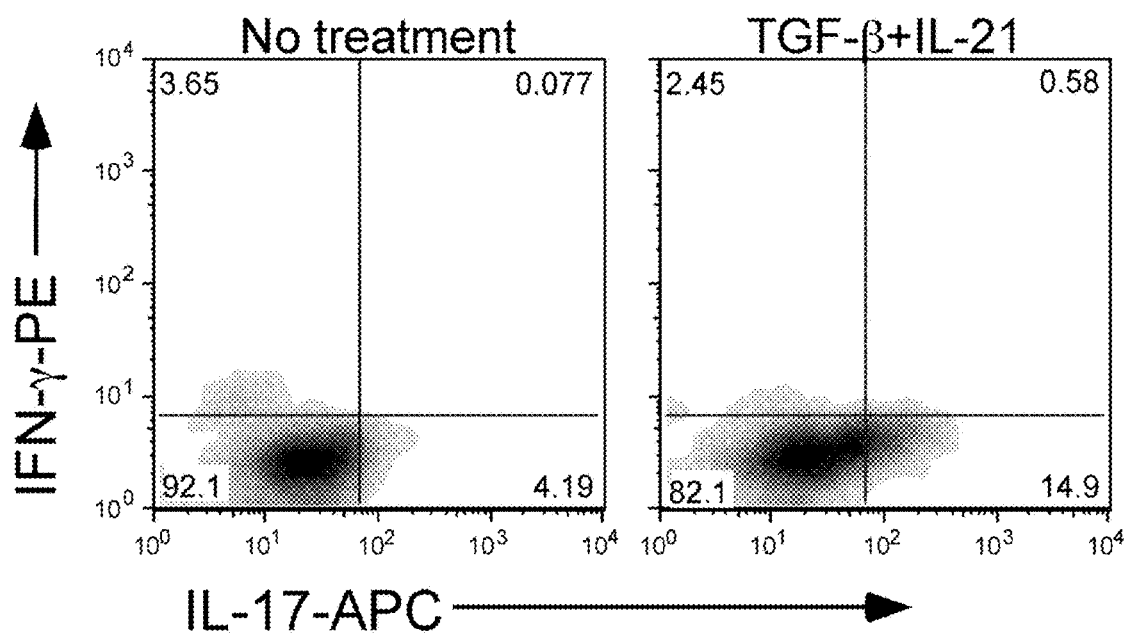

In marked contrast, a combination of TGF-β and IL-21 was uniquely able to induce TH17 differentiation. Whereas IL-21, IL-1β, or IL-6 induced significant amounts of IFN-β secretion from naïve T cells, the addition of TGF-β with IL-21 suppressed IFN-β secretion and induced differentiation of TH17 cells. Intracytoplasmic staining demonstrated, in agreement with ELISA results, that the combination of TGF-β and IL-21 differentiated CD4+ T cells that secreted only IL-17A and no IFN-β (FIG. 1C). When starting with FACS-isolated naïve CD4+ T cells, between 10%-15% of CD4+ T cells secrete IL-17A after just seven days of differentiation.

Figure 2A:
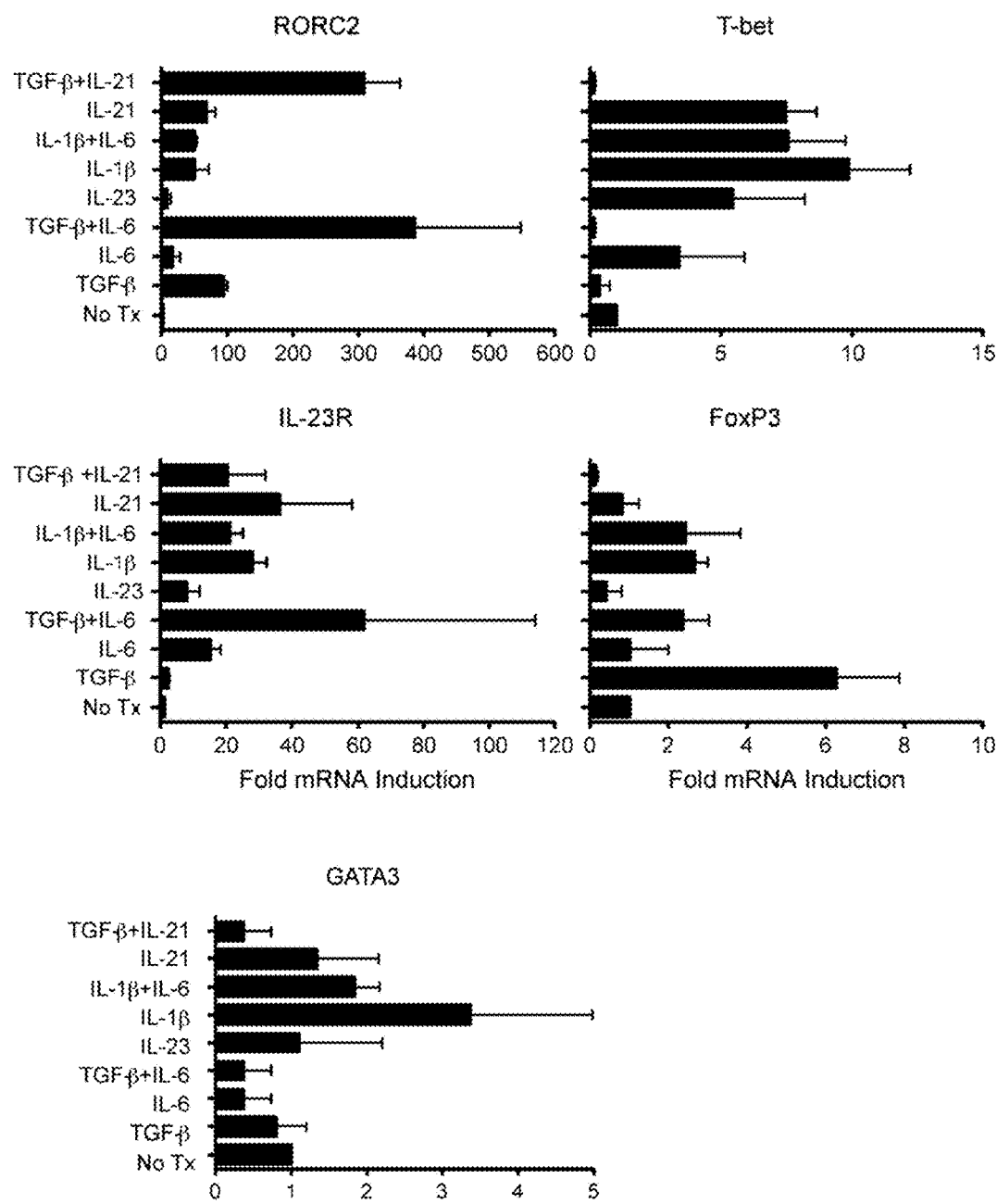
FIGS. 2A to 2D demonstrate that TGF-β and IL-21 induces RORC2 in naïve CD4$^+$ T cells.

In the murine model, TH17 differentiation coincides with expression of murine RORγt, a transcription factor critical for the differentiation of murine IL-17-secreting T cells. RORC2 is the human homologue of murine RORγt, thus, quantitative RT-PCR was used to evaluate mRNA levels of RORC2 and other molecules implicated in TH17 differentiation. The combination of TGF-β and IL-21 induced high levels of RORC2 (FIG. 2A), consistent with their ability to induce IL-17A secretion from naïve human CD4+ T cells. It was of particular interest that the combination of TGF-β and IL-6 that induces TH17 differentiation in murine T cells also induced expression of RORC2 in naïve human CD4 cells. As this combination of cytokines did not, however, induce IL-17A secretion, these data indicate that expression of RORC2 in humans is not in itself sufficient to induce IL-17 production and another as yet unidentified transcription factor in combination with RORC2 may be required to induce IL-17A-secreting TH17 cells.

Additional transcription factors implicated in TH1 and TH2 cell differentiation were also examined: T-bet is the master regulator for IFN-γ secreting TH1 cells, and GATA-3 induces IL-4 secreting TH2 cells. mRNA expression levels of T-bet were highly concordant with amounts of IFN-γ secretion and were consistent with findings that although TGF-β and IL-21 induce TH17 cell differentiation with RORC2 expression, TGF-β suppresses the induction of T-bet by IL-21. Similarly, there was no induction of GATA-3 with TGF-β and IL-21. The cytokines IL-6, IL-21 and IL-1β, but not TGF-β, induced IL-23 receptor up-regulation in stimulated naïve CD4+ T cells. The expression of the Treg transcription factor FoxP3 was also examined. As has been previously reported in both murine and human systems, FoxP3 was induced by TGF-β. This induction of FoxP3 was inhibited by both IL-6 and to a greater extent IL-21, transcription factors that induce RORC2. Thus, although the induction of RORC2 and FoxP3 transcription factors was highly similar between murine and human naïve CD4 cells, the induction of IL-17A by IL-6 in combination with TGF-β is discordant between the species.

Figure 2B:
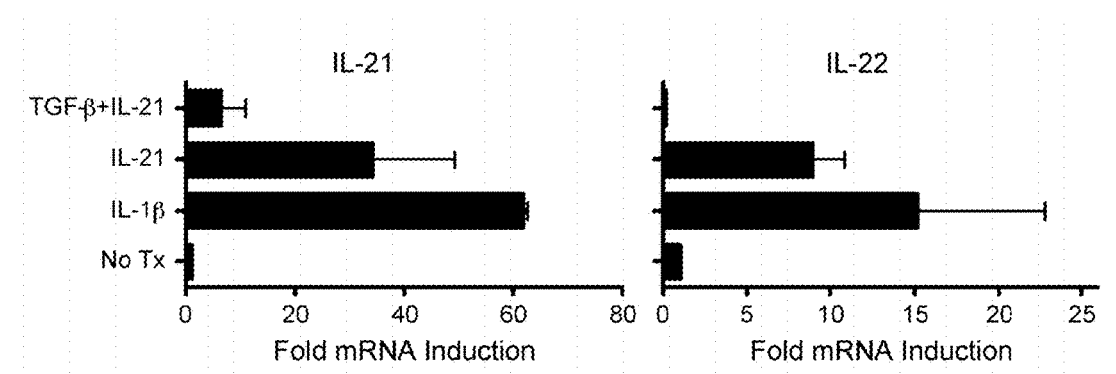

It was shown previously that IL-21 secreted by murine CD4+ T cells can induce the secretion of IL-21 in an autocrine loop. Korn et al., 2007; Nurieva et al., 2007; Zhou et al., 2007; Weo et al., 282 J. Biol. Chem. 34605-10 (2007). Thus, whether human IL-21 induced IL-21 secretion from naïve CD4+ T cells was evaluated, as were the effects of a combination of TGF-β with IL-21 and IL-1β, given the ability of these cytokines to induce IL-17 from naïve and central memory CD4+ T cells. Consistent with results observed in mice, IL-21 significantly up-regulated IL-21, though IL-1β induced even greater amounts of IL-21 mRNA (FIG. 2B). In contrast to what has been observed in mice, however, IL-21 also induced IL-22 mRNA levels in naïve CD4+ T cells in the absence of any exogenous IL-23. TGF-β, in contrast, suppressed the expression of IL-21 and IL-22 mRNA induced by IL-21 (FIG. 2B). These data further highlight differences between the CD4+ T cells of mice and men: although IL-21 induces IL-21 and IL-22, the T cell differentiation to TH17 cells with TGF-β inhibits the expression of these cytokines.

Figure 2C:
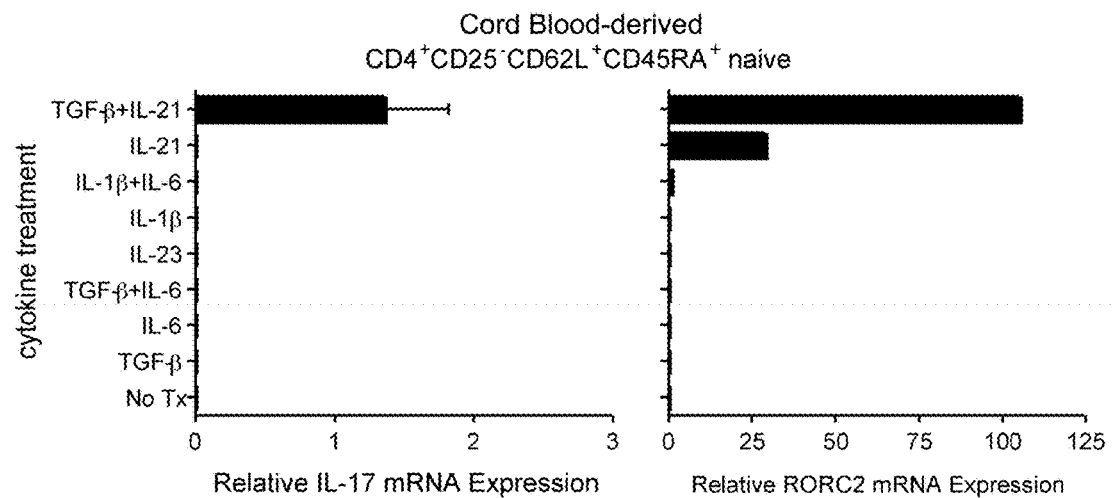
Figure 2D:
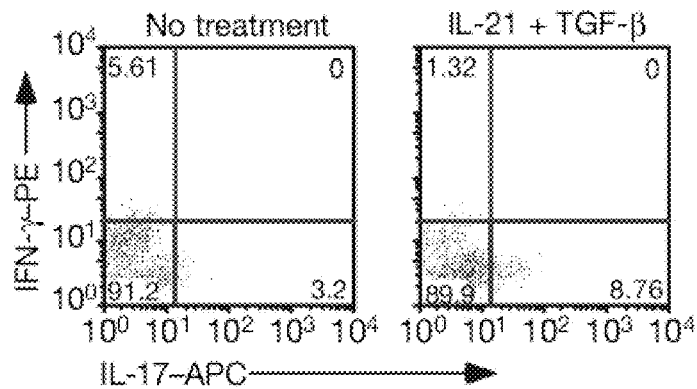

The unique function of TGF-β and IL-21 in the differentiation of TH17 cells from naïve human CD4+ T cells was confirmed by sorting CD4+ CD25− CD62L+ CD45RA$^{hi}$ cells from human cord blood. A higher proportion of CD4 cells in the cord blood exhibited this naïve phenotype relative to peripheral blood obtained from healthy adult subjects. Although it was difficult to detect IL-17A secretion from stimulated naïve cord blood T cells, TGF-β and IL-21 induced the up-regulation of IL-17A and RORC2 mRNA (FIG. 2C). Additionally, although IL-21 alone modestly induced RORC2, only TGF-β and IL-21 were able to induce IL-17A mRNA. These data further indicate that TGF-β and IL-21 are critical in the differentiation of both human and murine TH17 cells.

The present invention refines and extends the understanding of the regulation of IL-17A secretion from human CD4+ T cells, and defines the conditions required for human TH17 cell differentiation. IL-1β together with IL-6 or IL-23 can induce IL-17A secretion, but these cytokines induce IL-17A expression from human memory CD4+ T cells and not from human naïve CD4+ T cells. TGF-β and IL-21, in combination, is required for the differentiation of TH17 cells from human naïve T cells.

The explanation for disparate results reported previously in the literature may be due to either the failure to obtain sufficiently pure naïve T cells using magnetic bead isolation, or use of medium containing human serum which is known to contain substantial amounts of both IL-6 and TGF-β (Wilson et al., 2007), and the use of neutralizing antibodies against both IFN-β and IL-4 in addition to the cytokines listed above. Acosta-Rodriguez et al., 2007.

The present work suggests that the IL-1β and IL-6 induced during the early stages of an inflammatory response may act on memory T cells to promote IL-17 and IL-21 secretion, with induced IL-21 able to synergize with TGF-β to promote differentiation of TH17 cells from naïve CD4+ T cells. The general immunosuppressive properties of TGF-β may be responsible for suppression of IFN-γ induced by IL-21 or IL-6. Nevertheless, the simple lack of IFN-γ is not sufficient to promote TH17 differentiation from naïve CD4+ T cells as TH17 differentiation was not achieved with a combination of TGF-β and IL-6 when IFN-γ secretion was well-suppressed. A wide range of doses of TGF-β were examined, ranging from 1 ng/ml to 100 ng/ml, and, indeed, at high doses of TGF-β all differentiation/proliferation was suppressed. The FACS sorted naïve CD4+ T cells from both adult and cord blood, had little to no detectable FoxP3 expression. Moreover, IL-21 alone does not induce human TH17 differentiation, which requires the presence of TGF-β. Thus, these data indicate that IL-21 does not promote TH17 differentiation simply by suppressing TREG activity. Further, although it is possible that T cells may produce sufficient amounts of TGF-β to synergize with IL-21 to promote TH17 differentiation, the naïve CD4+ T cells represented herein did not produce sufficient amounts, as the addition of IL-21 alone was unable to synergize with endogenous levels of TGF-β to promote IL-17 secretion.

Ultimately, the experimental approach simultaneously comparing both naïve and memory cell populations in response to cytokine combinations allows the more definitive statements about the cell populations that respond to particular cytokines, as examined by others: that IL-1β and IL-6 induce IL-17 secretion from memory CD4+ T cells, and that TGF-β and IL-21 induce the differentiation of IL-17-secreting CD4+ T cells from naïve CD4+ T cells. The present invention now allows for the characterization of human inflammatory TH17 responses associated with infection and autoimmune diseases.

Thus, the present embodiments relate to methods and compositions for modulating TH17 cell differentiation and activity. The methods and compositions, e.g., agonists or antagonists of TGF-β and IL-21, described herein are useful in treating (e.g., curing, ameliorating, delaying or preventing the onset of, or preventing recurrence or relapse of), or preventing immune-associated ailments such as asthma, allergy, rheumatoid arthritis, multiple sclerosis, lupus, type I diabetes, Crohn's disease, psoriasis, myasthenia gravis, or other autoimmune disorders associated with TH17 differentiation.

In one embodiment, the method includes contacting a human T cell or human T cell population with TGF-β and IL-21 agonists in amount sufficient to induce differentiation of the T cell or T cell population into a TH17 cell or a TH17 cell population. Hence, a method of increasing TH17 cell activity and/or TH17 cell number is provided. For example, TH17 cell activity and/or cell number can be increased by increasing differentiation (e.g., differentiation of a naïve T cell) into a TH17 cell. The method includes (optionally) identifying a cell (a T cell), or a cell population, where increased differentiation is desired, and contacting said cell or cell population with a TGF-β/IL-21 agonists in an amount sufficient to increase differentiation into TH17 cells, thereby increasing TH17 cell activity and/or cell number.

In a related embodiment, the contacting step is carried out ex vivo, in vitro, or in vivo. In some embodiments, the contacting step is performed using mammalian or human cells, or performed in a patient such as a human patient. For example, immune cells, e.g., T cells as described herein, can be cultured in vitro in culture medium and the contacting step can be effected by adding one or more TGF-β/IL-21 modulators (TGF-β/IL-21 agonists or antagonists), to the culture medium. Alternatively, the method is performed on cells (such as immune or T cells) present in a subject as part of an in vivo (e.g., therapeutic or prophylactic) protocol.

The TGF-β agonist can be a TGF-β polypeptide, a human TGF-β polypeptide, or an active fragment thereof (e.g., a recombinant human TGF-β polypeptide or its encoding nucleic acid). The TGF-β agonist may be a fusion protein comprising an TGF-β polypeptide, e.g., human TGF-β polypeptide, or a fragment thereof fused to another polypeptide, e.g., an immunoglobulin polypeptide or a portion thereof (e.g., a Fc region of an immunoglobulin polypeptide); an agonist antibody to the TGF-β receptor TGF-βR); or a small molecule agonist. Human recombinant TGF-βs are available commercially (e.g., from Bioclone, Inc., San Diego, Calif., and R&D Systems, Minneapolis, Minn.). Reconstitution and transphosphorylation of recombinant TGF-βR complexes has also been reported. Ventura et al., 13(23) EMBO J. 5581-89 (1994). TGF-β expression may also be up-regulated using other cytokines, such as TNF-α. Sullivan et al., AJRCMB (Jan. 14, 2005).

The IL-21 agonist can be an IL-21 polypeptide, a human IL-21 polypeptide, or an active fragment thereof (e.g., a recombinant human IL-21 polypeptide or its encoding nucleic acid). The IL-21 agonist may be a fusion protein comprising an IL-21 polypeptide, e.g., human IL-21 polypeptide, or a fragment thereof fused to another polypeptide, e. g., an immunoglobulin polypeptide or a portion thereof (e.g., a Fc region of an immunoglobulin polypeptide); an agonist antibody to the IL-21 receptor IL-21R); or a small molecule agonist. Recombinant human IL-21 is available commercially, e.g., from Prospec Protein Specialists (Rehovot, Israel). Additionally, the nucleotide sequence and amino acid sequence of a human IL-21 is available at Genbank Acc. No. X_011082. Murine IL-21 polypeptides and nucleic acids encoding such polypeptides are exemplified in WO/2004/007682. In other embodiments, the IL-21 agonist is an agent that increases the activity or level of IL-21 by, e.g., increasing expression, processing and/or secretion of functional IL-21.

In another embodiment, the invention provides for a method for inhibiting precursor T cell or T cell population differentiation into a $T_H17$ cell or $T_H17$ cell population. The method includes contacting the T cell or T cell population with an antagonist of a TGF-β and IL-21, or a TGF-βR and IL-21R, in amounts sufficient to inhibit $T_H17$ cell differentiation. The TGF-β antagonist may be, for example, an anti-TGF-βR antibody, an antigen-binding fragment of an anti-TGF-βR antibody, or a soluble fragment of an TGF-βR. The IL-21 antagonist may be, for example, an anti-IL21R antibody, an antigen-binding fragment of an anti-IL21R antibody, or a soluble fragment of an IL-21R. Expression of TGF-β and IL-21 or their receptor genes may be suppress by RNA interference with, e.g., dsRNA, ssRNA, siRNA, miRNA, artificial derivatives of the forgoing, and the like.

TGF-β and IL-21 antagonists that inhibit a TGF-β/IL-21 mediated T helper cell effect, an agent that blocks or otherwise inhibits the interaction of TGF-β to a TGF-βR or IL-21 to an IL-21R can be added to a T cell or a population of T cells. These antagonists include, e.g., soluble fragments of TGF-β or IL-21 polypeptide, TGF-βR or IL-21R fragments, fusion proteins containing these fragments, and antibodies to these fragments.

Antibodies include all such classes, subclasses and types of human antibody species. For example, antibodies to TGF-β or TGF-βR polypeptides also include antibodies to fusion proteins containing TGF-β or TGF-βR polypeptides or fragments of TGF-β or TGF-βR polypeptides. Similarly, antibodies to IL-21 or IL-21R polypeptides also include antibodies to fusion proteins containing IL-21 or IL-21R polypeptides or fragments of IL-21 or IL-21R polypeptides.

More specifically, the TGF-β antagonist can be, e.g., an antibody (e.g., a monoclonal or single specificity antibody) to TGF-β or human TGF-β, or a TGF-βR polypeptide. The antibody may be human, humanized, chimeric, or in vitro generated antibody to human TGF-β or human TGF-βR polypeptides. In other embodiments, the antagonist includes a fragment of a TGF-β polypeptide, e.g., a TGF-β binding domain of a TGF-β polypeptide. Alternatively, the antagonist includes a fragment of a TGF-βR polypeptide, e.g., a TGF-β binding domain of a TGF-βR polypeptide. In one embodiment, the antagonist is a fusion protein comprising the aforesaid TGF-β or TGF-βR polypeptides or fragments thereof fused to a second moiety, e.g., a polypeptide (such as an immunoglobulin chain). Anti-TGF-β antibodies are available commercially, e.g., from Invitrogen Corp. (Carlsbad, Calif.), as are numerous antibodies targeting proteins involved in TGF-β signaling pathways. Agents that inhibit endogenous TGF-β include pirfenidone (Liu et al., 5 Am. J. Transplantation, 1266-63 (2005), or other compounds such as those described in U.S. Pat. No. 7,314,939. Agents that inhibit TGB-beta signaling, include Halofuginone (Figueiro-Ponts et al., 92(2) Haematologica 177 (2007)), Genistein, and curcumin (Santibanez et al., 37(1) Nutrition & Cancer, 49-54 (2000)).

Additional TGF-β Superfamily modulators include Amnionless NCAM-1/CD56, BAMBI/NMA Noggin, BMP-1/PCP NOMO, Caronte PRDC, Cerberus 1 SKI, Chordin Smad1, Chordin-Like 1 Smad2, Chordin-Like 2 Smad3, COCO Smad4, CRIM1 Smad5, Cripto Smad7, Crossveinless-2 Smad8, Cryptic SOST/Sclerostin, DAN Latent TGF-β bp1, Decorin Latent TGF-β bp2, Dermatopontin Latent TGF-β bp4, FLRG TMEFF1/Tomoregulin-1, Follistatin TMEFF2, Follistatin-like 1 TSG, GASP-1/WFIKKNRP TSK, GASP-2/WFIKKN Vasorin, Gremlin, from R&D Systems (Minneapolis, Minn.).

The IL-21 antagonist can be, e.g., an antibody (e.g., a monoclonal or single specificity antibody) to IL-21 or human IL-21, or an IL-21R polypeptide. The antibody may be human, humanized, chimeric, or in vitro generated antibody to human IL-21 or human IL-21R polypeptides. In other embodiments, the antagonist includes a fragment of an IL-21 polypeptide, e.g., an IL-21R binding domain of an IL-21 polypeptide. Alternatively, the antagonist includes a fragment of an IL-21R polypeptide, e.g., an IL-21 binding domain of an IL-21R polypeptide. In one embodiment, the antagonist is a fusion protein comprising the aforesaid IL-21 or Il-21R polypeptides or fragments thereof fused to a second moiety, e.g., a polypeptide (such as an immunoglobulin chain).

For example, IL-21 modulators available commercially include human IL-21R, recombinant human IL-21R/Fc chimera, human IL-21R Allophycocyanin MAb, human IL-21R Biotinylated PAb, human IL-21R MAb, and human IL-21R Phycoerythrin MAb, from R&D Systems (Minneapolis, Minn.). Other agents may serve as antagonists of IL-21 gene expression. For example, cyclosporine inhibits the IL-21 promoter. Kim et al., 280 (26) J. Biol. Chem. (2005). Other IL-21 antagonists are reported in U.S. Pat. No. 7,186,805 and No. 6,929,932, relating to IL-21 mutants that bind IL-21R.

In another embodiment, the invention features a method for modulating, e.g., increasing, or reducing or inhibiting, the activity or level of cytokines, such as IFN-γ or IL-17, in human a T cell or human T cell population. For example, a method for modulating one or more of: IL-17 activity, expression, secretion, or processing, in a T cell or a $T_H17$ cell, or a cell population thereof, is provided. The method includes: (optionally) identifying a cell in which modulation (increase or reduction) of the activity or level of IL-17 is desired; and contacting said cell or cell population with an amount of TGF-β/IL-21 modulators, e.g., TGF-β/IL-21 agonists or antagonists, sufficient to modulate the activity or level of IL-17 in said cell or cell population. As noted, the contacting step may be carried out ex vivo, in vitro, or in vivo. For example, the contacting step may be performed using human cells, or performed in a human patient.

Notably, the TGF-β/IL-21 modulators discussed herein may specifically inhibit IL-17 levels or activity, but may also reduce or inhibit the activity or level of other cytokines associated with IL-17 expression or Th17 functionality. For example, the TGF-β/IL-21 agonists inhibit production of IFN-γ by an IFN-γ-producing cell such as a T$_H$1 cell.

The TGF-β polypeptide or TGF-βR polypeptide moiety may be variant TGF-β or TGF-βR polypeptide having mutations in the naturally-occurring TGF-β or TGF-βR sequence (wild type) that results in an TGF-β or TGF-βR sequence more resistant to proteolysis (relative to the non-mutated sequence). Likewise, the IL-21 polypeptide or IL-21R polypeptide moiety may be a variant IL-21 or IL-21R polypeptide having mutations in the naturally-occurring IL-21 or IL-21R sequence (wild type) that results in an IL-21 or IL-21R sequence more resistant to proteolysis (relative to the non-mutated sequence).

TGF-β, TGF-βR, IL-21 and IL-21R, or active fragments of these proteins, can be fused to carrier molecules such as immunoglobulins for use in the herein described methods. For example, soluble forms of the receptor may be fused through "linker" sequences to the Fc portion of an immunoglobulin or to the Fc portion of the immunoglobulin. Other fusions proteins, such as those with glutathione S-transferase (GST), LexA, or maltose binding protein (MBP), may also be used.

In a further embodiment, TGF-β, TGF-βR, IL-21 or IL-21R fusion protein may be linked to one or more additional moieties. For example, the fusion protein may additionally be linked to a GST fusion protein in which the fusion protein sequences are fused to the C-terminus of the GST sequences. Such fusion proteins can facilitate the purification of the TGF-β, TGF-βR, IL-21 or IL-21R fusion proteins.

In another embodiment, the fusion protein includes a heterologous signal sequence (i.e., a polypeptide sequence that is not present in a polypeptide naturally encoded by TGF-β, TGF-βR, IL-21 or IL-21R nucleic acid) at its N-terminus. For example, the native signal sequence can be removed and replaced with a signal sequence from another protein.

A chimeric or fusion protein of the invention can be produced by standard recombinant DNA techniques. For example, DNA fragments coding for the different polypeptide sequences are ligated together in-frame in accordance with conventional techniques, e. g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers.

As noted, the methods described herein may be used on cells, e.g., T cells, in vitro or ex vivo. Alternatively, the method can be performed on cells present in a subject as part of an in vivo (e.g., therapeutic or prophylactic) protocol. For example, the method can be used to treat or prevent a T$_H$17-mediated disorder in a subject. Accordingly, the invention provides a method of treating (e.g., curing, suppressing, ameliorating, delaying or preventing the onset of, or preventing recurrence or relapse of) or preventing a T$_H$17-associated disorder in a subject. The method includes administering to a subject a TGF-β/IL-21 antagonists in an amount sufficient to inhibit or reduce T$_H$17 cell activity and/or cell number, thereby treating or preventing a T$_H$17-associated disorder.

The subject is a mammal, such as a human suffering from a disorder associated with aberrant T$_H$17 cell number or activity, e.g., an immune disorder. The amount sufficient to inhibit or reduce the T$_H$17 cell activity and/or T$_H$17 cell number is an amount sufficient to ameliorate or prevent said disorder.

The TGF-β/IL-21 modulators effective in the present invention, more particularly the chemical agents or compounds that serve as agonists or antagonists, include pro-drugs. The term "pro-drug" refers to any compound which releases an active parent drug in vivo when such pro-drug is administered to a mammalian subject. Pro-drugs of a compound are typically prepared by modifying one or more functional group(s) present in the compound in such a way that the modification(s) may be cleaved in vivo to release the parent compound. Examples of pro-drugs include, but are not limited to, esters (e.g., acetate, formate, and benzoate derivatives) and carbamates (e.g., N,N-dimethylaminocarbonyl) of hydroxy functional groups, and amides, carbamates and urea derivatives of amino functional groups, and the like. Pro-drug forms often offer advantages of solubility, tissue compatibility, or delayed release in the mammalian organism. See Bundgard, DESIGN OF PRODRUGS, 7-9, 21-24 (Elsevier, Amsterdam, 1985); Silverman, ORGANIC CHEM. OF DRUG DESIGN & DRUG ACTION, 352-401 (Academic Press, San Diego, Calif.). Moreover, the prodrug derivatives of the invention may be combined with other features known to one skilled in the art to enhance bioavailability.

The TGF-β/IL-21 modulators described herein can be conveniently provided in pharmaceutical compositions. The compositions may be suitable for internal use and include an effective amount of the pharmacologically active compounds of the invention, alone or in combination, with one or more pharmaceutically acceptable carriers. The compounds are especially useful in that they have very low, if any toxicity. In practice, the compounds or their pharmaceutically acceptable salts, are administered in amounts which will be sufficient to effect the desired change, such as an increase or decrease T$_H$17 cell differentiation, and are used in the pharmaceutical form most suitable for such purposes.

For pharmaceutical use, the proteins of the present invention are formulated for parenteral, particularly intravenous or subcutaneous, delivery according to conventional methods. The bioactive polypeptide or antibody conjugates described herein can be delivered intravenously, intraarterially or intraductally, or may be introduced locally at the intended site of action. Intravenous administration will be by bolus injection or infusion over a typical period of one to several hours. In general, pharmaceutical formulations will include a IL-21 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in REMINGTON: SCI. & PRACTICE OF PHARMACY (Gennaro, ed., Mack Pub. Co., Easton, Pa., 19th ed., 1995). Therapeutic doses may generally be in the range of 0.1 μg/kg to 100 μg/kg of patient weight per day, such as 0.5 μg/kg-20 μg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of the TGF-β/IL-21 modulators is an amount sufficient to produce a clinically significant change in hematopoietic or immune function For instance, for oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1% to 75%, such as about 1% to 50%, of the active ingredient. More specifically, any of the pharmaceutical compositions discussed herein may contain 0.1% to 99%, such as 1% to 70% of the TGF-β/IL-21, TGF-βR/IL-21R, TGF-β/IL-21 agonists, or TGF-β/IL-21 antagonists.

The compounds of the invention can also be administered in such oral dosage forms as timed release and sustained release tablets or capsules, pills, powders, granules, elixers, tinctures, suspensions, syrups and emulsions.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

The compounds of the invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795.

Furthermore, compounds for the invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would range from 0.1% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The compounds of the invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Compounds of the invention may also be delivered by the use of monoclonal antibodies as individual carriers to which the compound molecules are coupled. The compounds of the invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the compounds of the invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Alternatively, where the complete gene delivery vector can be produced intact from recombinant cells, e.g., retroviral vectors, the pharmaceutical preparation can include one or more cells that produce the gene delivery system.

If desired, the pharmaceutical composition to be administered may also contain minor amounts of non-toxic auxiliary substances such as wetting or emulsifying agents, pH buffering agents, and other substances such as for example, sodium acetate, triethanolamine oleate, etc.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the invention, when used for the indicated effects, will range between about 0.05 mg/day to 1000 mg/day orally. Effective plasma levels of the compounds of the invention range from 0.002 mg to 50 mg per kg of body weight per day. Compounds of the invention may be administered in a single daily dose, or the total daily dosage may be administered in divided doses of two, three or four times daily.

A further embodiment of the present invention provides for a method for modulating the activity of a T$_H$17 cell or T$_H$17 cell population comprising contacting said cell or cell population with an amount of T$_H$17 activity modulator sufficient to modulate the activity of a T$_H$17 cell or T$_H$17 cell population. For example, the migration activity of T$_H$17 cells may be inhibited by U75-302, an antagonist of the T$_H$17-specific leukotriene B4. Similarly, the migration activity of T$_H$17 cells may be inhibited by podoplanin. Such T$_H$17-activity-specific modulators may be formulated according to the foregoing discussions for use in vitro and in vivo.

Figure 6:
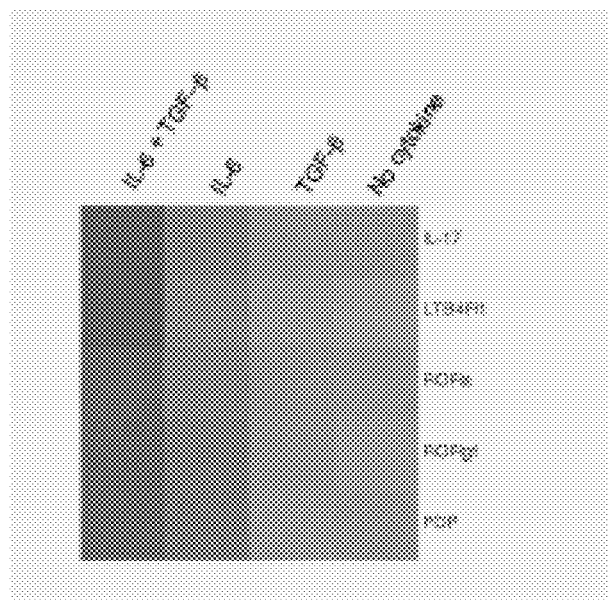
FIG. 6 is a heat map of gene expression profiling from naïve CD4$^+$ T cells activated in the presence of no cytokine, IL-6, TGF-β, and TGF-β plus IL-6 (TH17 cells). Naïve CD4$^+$ T cells from C57BL/6 mice were stimulated with anti-CD3 and anti-CD28 antibodies in the presence of the different cytokines indicated. mRNA was from these different populations was prepared after three days and gene expression profiling was performed with AFFYMETRIX® chips (Santa Clara, Calif.).

The present invention also provides for the identification of T$_H$17 cells via cell surface molecules that are specifically up-regulated in T$_H$17 cells. More specifically, expression profiling comparing naïve T cells differentiated into T$_H$17 cells with T cells cultured in the presence of either IL-6 alone or TGF-β alone identified genes expressed specifically in T$_H$17 cells (differentiated in the presence of TGF-β plus IL-6) but not in naïve T cells activated in the presence of IL-6, TGF-β, or no cytokines. Consistent with published literature, IL-17A and the transcription factors RORγt and RORα were up-regulated in T$_H$17 cells compared to cells cultured in other conditions. Ivanov et al., 126 Cell 1121-33 (2006); Yang et al., Immunity (2007). Two surface molecules: BLT1 (LTB4R1) (the receptor for the leukotriene B4), and podoplanin are specifically up-regulated in T$_H$17 cells (FIG. 6).

Using the markers of the present invention, T$_H$17 cells may be identified in a sample. The "sample" or "biological sample" may be any biological material taken either directly from a subject human being (or animal), or after culturing (enrichment). Biological material may include expectorations of any kind, broncheolavages, blood, skin tissue, biopsies, semen, lymphocyte blood culture material, colonies, liquid cultures, faecal samples, urine, etc. Biological material may also include cell cultures or the liquid phase thereof. The term "biological sample" generally refers to any biological sample (tissue or fluid) containing T$_H$17 cells, and includes blood serum or plasma samples.

The sample may be collected from a subject, which refers to an individual regardless of health and/or disease status. A subject can be a patient, a study participant, a control subject, a screening subject, or any other class of individual from whom a sample is obtained and assessed in the context of the invention. A subject can be diagnosed with a disease, can present with one or more symptom of a disease, or a predisposing factor, such as a family (genetic) or medical history (medical) factor, for a disease. Alternatively, a subject can be healthy with respect to any of the aforementioned factors or criteria, although the term "healthy" is relative to a specified disease, or disease factor, or disease criterion, and can not be defined to correspond to any absolute evaluation or status. Thus, an individual defined as healthy with reference to any specified disease or disease criterion, can in fact be diagnosed with any other one or more disease, or exhibit any other one or more disease criterion.

Additionally, although the discussion of the invention focuses on, and is exemplified using human and murine cells and markers, the particular markers may be applicable to other non-human animals and have use in research and veterinary practice.

The T$_H$17 cell-specific markers of the present invention can be identified by antibodies. Such antibodies can include, but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Such antibodies can be used, for example, in the detection T$_H$17 markers in a biological sample, or, alternatively, as a modulator to T$_H$17 functionality as described herein. Thus, such antibodies can be utilized as part of autoimmune or other disease treatment methods, and/or can be used as part of diagnostic techniques whereby patients may be tested for abnormal levels of T$_H$17-specific markers.

A number of protocols for carrying out immunoassays are known, which can, for example, be based upon competition, or direct reaction, or sandwich assays. Protocols can use solid supports or immunoprecipitation. Immunoassays generally involve the use of labeled antibody or polypeptide. The labels can be, for example, fluorescent, chemiluminescent, radioactive, or dye molecules. A particular aspect of the invention provides for molecules capable of recognizing podoplanin and/or BLT1, attached to a substrate.

The markers of the present invention can also be identified by assessing their expression via nucleic acid molecules. Numerous methods for obtaining expression data are known, and any one or more of these techniques, singly or in combination, are suitable for determining expression profiles in the context of the present invention. For example, expression patterns can be evaluated by northern analysis, PCR, RT-PCR, Taq Man analysis, FRET detection, monitoring one or more molecular beacons, hybridization to an oligonucleotide array, hybridization to a cDNA array, hybridization to a polynucleotide array, hybridization to a liquid microarray, hybridization to a microelectric array, cDNA sequencing, clone hybridization, cDNA fragment fingerprinting, serial analysis of gene expression (SAGE), subtractive hybridization, differential display and/or differential screening. See, e.g., Lockhart & Winzeler 405 Nature 827-36 (2000); U.S. Pat. No. 6,905,827.

The present invention also provides a kit for the identification of T$_H$17 cells. Typically, a kit contains one or more probes, such as antibodies or diagnostic nucleotides. The probe can exist as part of a diagnostic nucleotide probe set, or other subset of a candidate library, (e.g., as a cDNA, oligonucleotide, or antibody microarray or reagents for performing an assay on a diagnostic gene set using any expression profiling technology), packaged in a suitable container. The kit can further comprise, one or more additional reagents, e.g., substrates, labels, primers, for labeling expression products, tubes and/or other accessories, reagents for collecting blood samples, buffers, e.g., erythrocyte lysis buffer, leukocyte lysis buffer, hybridization chambers, cover slips, etc., as well as a software package, e.g., including the statistical methods of the invention, e.g., as described above, and a password and/or account number for accessing the compiled database. The kit optionally further comprises an instruction set or user manual detailing preferred methods of using the diagnostic probes in the methods of the invention.

The methods and kits for identifying T$_H$17 cells can be used to identify or determine (qualitatively or quantitatively) if a subject (e.g., and patient or individual) has T$_H$17 cells. In some instances, T$_H$17 cells may be associated with an autoimmune disorder. An autoimmune disorder is defined as a disease state in which a patient's immune system recognizes an antigen in that patient's organs or tissues as foreign and becomes activated. The activated immune cells can then cause damage to the inciting organ or tissue or can damage other organs or tissues. In some cases, the disorder may be caused by a dysregulation of the immune system cells, rather than by the recognition as a self-antigen as foreign. Dysregulated immune cells can secrete inflammatory cytokines that cause systemic inflammation or they can recognize self-antigens as foreign.

Examples of autoimmune diseases include autoimmune hepatitis, multiple sclerosis, myasthenia gravis, Type I diabetes, rheumatoid arthritis, psoriasis, systemic lupus erythematosis, Hashimoto's thyroiditis, Grave's disease, ankylosing spondylitis Sjogrens disease, CREST syndrome, and scleroderma. Most of the autoimmune diseases are also chronic inflammatory diseases. This is defined as a disease process associated with long-term (>6 months) activation of inflammatory cells (leukocytes). The chronic inflammation leads to damage of patient organs or tissues. Many diseases are chronic inflammatory disorders, but are not know to have an autoimmune basis. Examples include atherosclerosis, congestive heart failure, Crohn's disease, ulcerative colitis, polyarteritis nodosa, Whipple's Disease, and primary sclerosing cholangitis.

The identification of $T_H17$ cells can be useful in monitoring individuals with autoimmune disorders. Monitoring describes the observation of $T_H17$ cell markers to provide useful information about an individual or an individual's health or disease status. "Monitoring" can include determination of prognosis, risk-stratification, selection of drug therapy, assessment of ongoing drug therapy, prediction of outcomes, determining response to therapy, diagnosis of a disease or disease complication, following progression of a disease or providing any information relating to a patients health status.

Further regarding rheumatoid arthritis (RA), the $T_H17$-specific cell surface molecules of the present invention can be used in the diagnosis and monitoring of RA. RA effects about two million patients in the U.S. and is a chronic and debilitating inflammatory arthritis, particularly involving pain and destruction of the joints. RA often goes undiagnosed because patients may have no pain, but the disease is actively destroying the joint. Other patients are known to have RA, and are treated to alleviate symptoms, but the rate of progression of joint destruction is not monitored easily. Drug therapy is available, but the most effective medicines are toxic (e.g., steroids, methotrexate) and should be used with caution. A new class of medications, TNF blockers, is effective, but the drugs are expensive, have side effects, and not all patients respond.

RA disease criteria correspond to disease symptoms (e.g., joint pain, joint swelling and joint stiffness and any of the American College for Rheumatology criteria for the diagnosis of RA, see Arnett et al., 31 Arthr. Rheum. 315-24 (1988), progression of joint destruction (e.g., as measured by serial hand radiographs, assessment of joint function and mobility), surgery, need for medication, additional diagnoses of inflammatory and non-inflammatory conditions, and clinical laboratory measurements including complete blood counts with differentials, CRP, ESR, ANA, Serum IL6, Soluble CD40 ligand, LDL, HDL, Anti-DNA antibodies, rheumatoid factor, C3, C4, serum creatinine, death, hospitalization, and disability due to joint destruction. In addition, or alternatively, disease criteria correspond to response to drug therapy and presence or absence of side-effects or measures of improvement exemplified by the American College of Rheumatology "20%" and "50%" response/improvement rates. See Felson et al., 38 Arthr. Rheum. 531-37 (1995). The $T_H17$ markers of the instant invention identify, monitor, and predict disease progression including flaring (acute worsening of disease accompanied by joint pain or other symptoms), response to drug treatment and likelihood of side-effects.

In conclusion, $T_H17$ cells are potent inducers of inflammation and autoimmune diseases. $T_H17$ cells are found in the target organs of many autoimmune diseases. Until the present invention, however, the absence of known markers on surface of these cells has not allowed the detection and isolation of live $T_H17$ cells from tissues and therefore the characterization of their effector function during autoimmune diseases. The identification of molecules such as BLT1 and podoplanin, specifically expressed on the surface of $T_H17$ cells, will greatly aid basic research regarding these cells, and diagnosis of $T_H17$-associated illness such as multiple sclerosis, psoriasis, rheumatoid arthritis and Crohn's disease.

The following examples illustrate various methods for compositions in the treatment method of the invention. The examples are intended to illustrate, but in no way limit, the scope of the invention.

EXAMPLES

Example 1 $T_H17$ Differentiation, Materials and Methods

Cell Sorting:

PBMCs were obtained from the peripheral blood of healthy subjects or from cord blood (AllCells) in compliance with institutional IRB protocols. CD4+ T cells were subsequently isolated by negative selection using magnetic beads (Miltenyi Biotech Inc., Auburn, Calif.). Naïve ($CD25^-$ $CD62L^+$ $CD45RA^{hi}$) and central memory ($CD25^-$ $CD62L^+$ $CD45RA^-$) $CD4^+$ T cells were obtained by staining with the following antibodies: CD62L-FITC, CD4-PerCP, CD45RA-PE-Cy7, CD25-APC-Cy7 (BD Pharmingen, San Diego, Calif.) and were sorted on a FACS Aria (BD Biosciences, Palo Alto, Calif.).

Differentiation Assays:

Naïve or central memory $CD4^+$ T cells were stimulated with plate-bound anti-CD3 and soluble CD28 monoclonal antibodies (1 µg/ml, each) in serum-free X-VIVO15 medium (Biowhittaker Inc., Walkersville, Md.) and cytokines (IL-6, 25 ng/ml; TGF-β, 5 ng/ml; IL-1β, 12.5 ng/ml; IL-21, 25 ng/ml; IL-23, 25 ng/ml) for a period of seven days, at which point supernatants were collected and tested by ELISA for IFN-β (BD Biosciences) or IL-17A (eBioscience, San Diego, Calif.) using paired antibodies. Intracytoplasmic staining was performed using standard methodologies and anti-IL-17-APC (R&D Systems, Minneapolis, Minn.) and anti-IFN-β-PE (BD Biosciences) antibodies.

Real-Time PCR:

All primers and probes were obtained from Applied Biosystems (Foster City, Calif.), and used according to standard methodologies.

Antibodies:

Antibodies recognizing podoplanin are available commercially from, for example, Abcam Inc. (Cambridge, Mass.) and Santa Cruz Biotechnology, Inc. (Santa Cruz, Calif.). Antibodies to LTB4R1 are available commercially from, for example, Sigma-Aldrich (St. Louis, Mo.) and R&D Systems (Minneapolis, Minn.). The anti-BLT1

(LTB4R1):FITC conjugated mAb (202/7B1) was obtained from AbD Serotec (Raleigh, N.C.). See Petersson, et al. (2000) 279 Biochem. Biophys. Res. Commun. 520-25 (2000). The anti-podoplanin antibody used in FACS staining was Rat monoclonal 8F11 obtained from MBL International (Woburn, Mass.). See Watanabe et al., 48 Cancer Res. 6411-16 (1988). The anti-podoplanin antibody used for in vivo injection was designated 8.1.1., obtained from Studies Hybridoma Bank, University of Iowa (Iowa City, Iowa). See Farr et al., J. Histochem. & Cytochem. (1992); Farr et al., J. Exp. Med. (1992).

Example 2. BLT1 Expression is Specifically Up-Regulated in TH17 Cells

Leukotriene B4 (LTB4), a degradation product of arachidonic acid and a potent lipid inflammatory mediator generated rapidly at the site of inflammation, is derived from membrane phospholipids by the sequential actions of cytosolic phospholipase A2 (PLA2), 5-lipoxygenase (5-LO), and LTA4 hydrolase. Jala & Haribabu, 25 Trends Immunol. 315-22 (2004). LTB4 is a potent chemoattractant that triggers the adherence and aggregation of leukocytes to the endothelium and recruits granulocytes and macrophages to the inflammation site. Recent studies have shown that LTB4 may also function as a chemoattractant for T cells. Goodarzi et al., 4 Nat. Immunol. 965-73 (2003); Tager et al., 4 Nature Immunol. 982-90 (2003); Tager & Luster, 69 Prostaglandins, Luekot. Essential Fatty Acids 123-34 (2003); Medoff et al., 202 J. Exp. Med. 97-110 (2005); Miyahara et al., 174 J. Immunol. 4979-85 (2005); Miyahara et al., 172 Am. J. Critical Care Med. 161-70 (2005).

Figure 7:
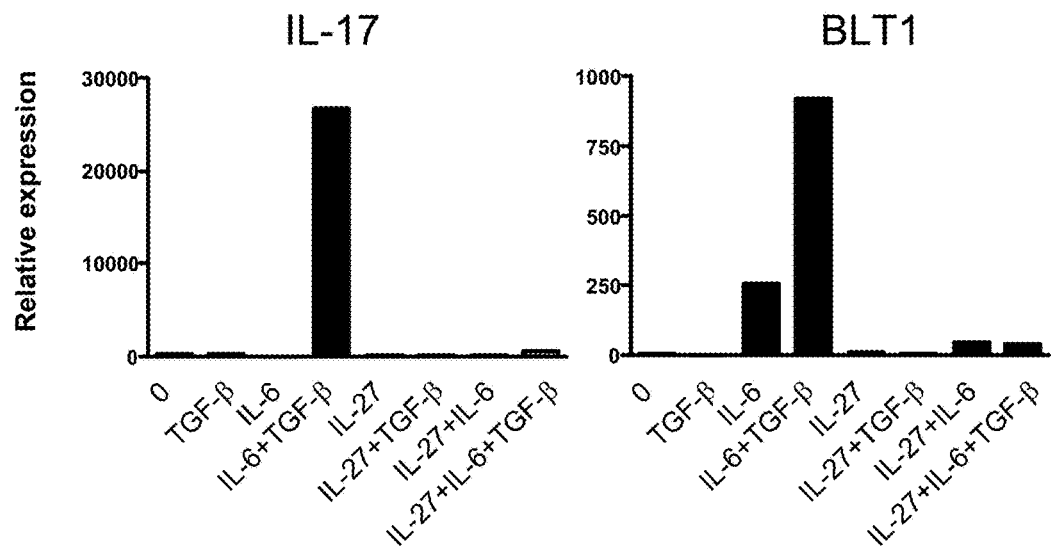
FIG. 7 shows the relative expression of BLT1 in naïve CD4$^+$ T cells stimulated in the presence of different cytokines. Naïve CD4$^+$ T cells from C57Bl/6 mice were stimulated with anti-CD3 and anti-CD28 in the presence of different cytokines. IL-17 and BLT1 mRNAs relative expression was determined by real time PCR, with specific primers and probes after three days of in vitro culture.
Figure 8:
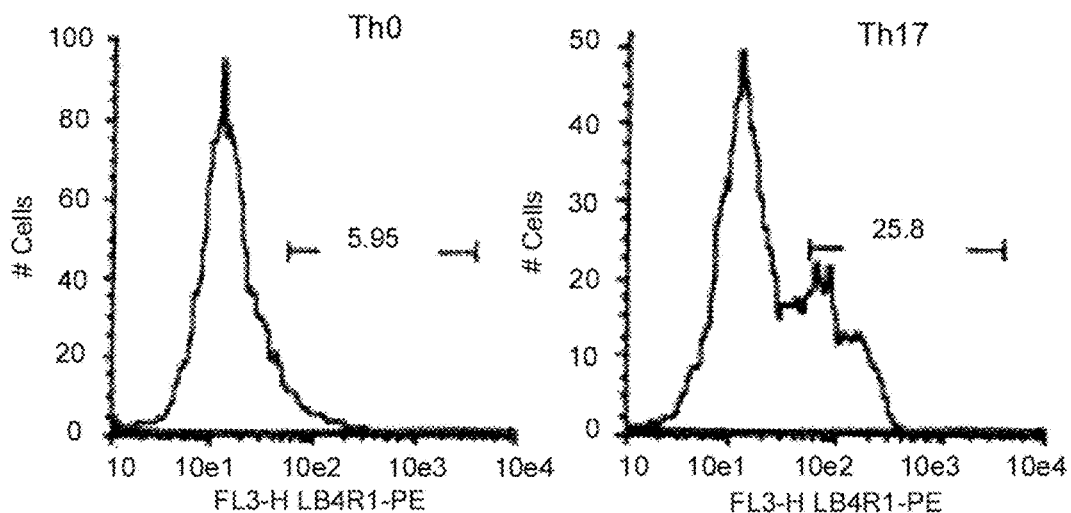
FIG. 8 shows the expression of BLT1 on CD4$^+$ human T cells stimulated in the presence of either no cytokine, or IL-21 plus TGF-β to induce human TH17 cells.
Figure 9:
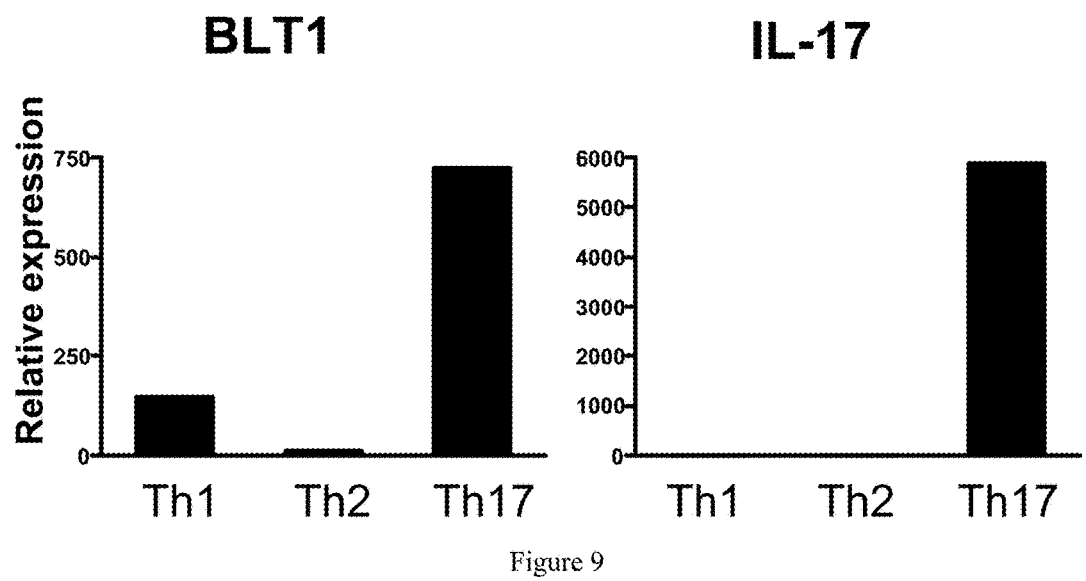
FIG. 9 is a bar graph indicating the BLT1 and IL-17 expression in TH subsets. Naïve CD4$^+$ T cells were stimulated with anti-CD3 and anti-CD28 in the presence of IL-12 and anti-IL-4 for TH1 cells, IL-4 and anti-IFN-γ for TH2 cells and IL-6 and TGF-β for TH17.

Gene expression profiling data showed that BLT1 is selectively induced by the combination of IL-6 and TGF-β, which also induces IL-17 (FIG. 7) and leads to the generation of TH17 cells. In order to determine whether the expression of BLT1 could also be observed in human TH17 cells, naïve CD4$^+$ T cells taken from healthy donors and activated with anti-CD3 and anti-CD28 in the presence of a combination of IL-21 and TGF-β, which induces the differentiation of TH17 cells in human cells, were analyzed the surface expression of BLT1 with a BLT1-specific antibody. In the absence of TH17-differentiating cytokines, only 5% of T cells expressed the BLT1 (FIG. 8). When human CD4 T cells were differentiated in the presence of IL-21 plus TGF-β, however, some of the CD4$^+$ T cells expressed BLT1. This shows for the first time that that both BLT1 mRNA and protein are rapidly and specifically expressed on mouse and also human TH17 cells. It may be noted that this selective expression on TH17 cells may be restricted to BLT1: the expression of BLT2 was not observed on TH17 cells but was observed on TH2 cells.

Example 3. Podoplanin Expression is Specifically Up-Regulated in TH17 Cells

Figure 10:
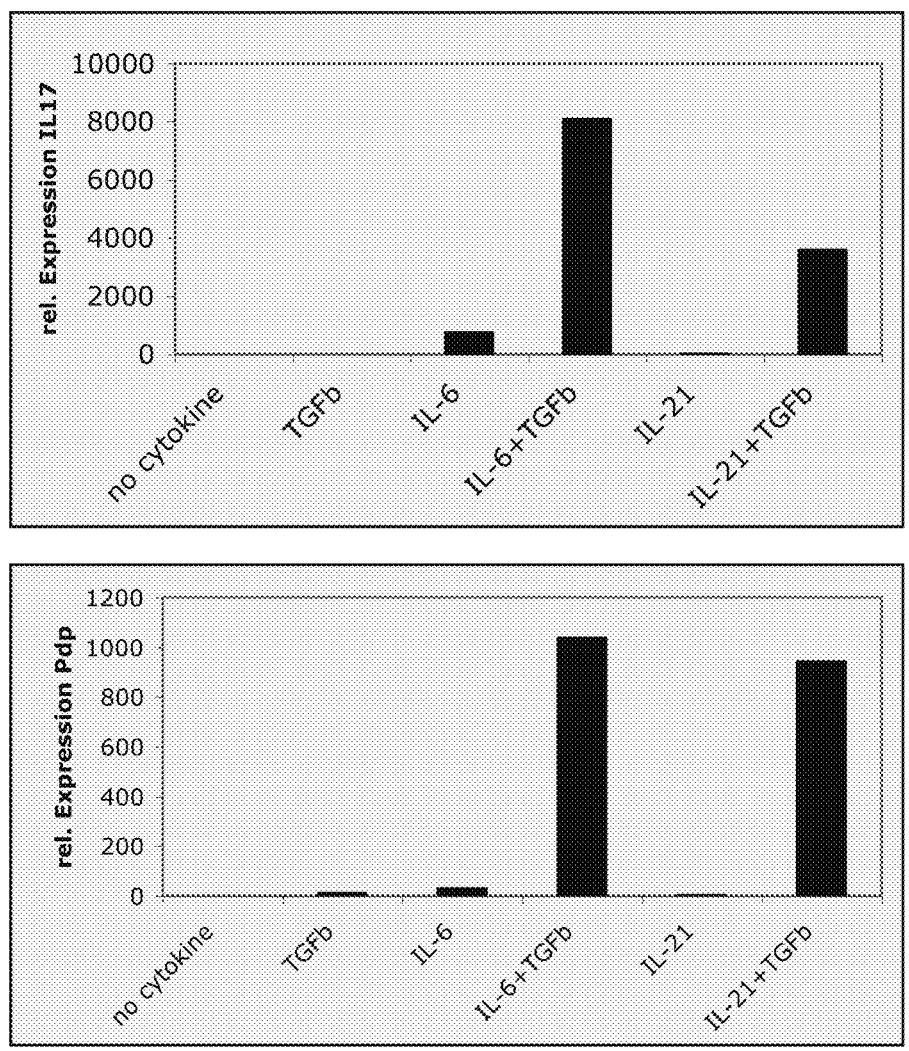
FIG. 10 presents data on the relative expression of IL-17 and podoplanin in CD4$^+$ T cells stimulated in the presence of different cytokines.

Podoplanin (PDP) is another surface molecule identified specifically on Th17 cells. Podoplanin is a transmembrane mucin-containing molecule, which is expressed on the lymphatic endothelium and tumor cells under pathogenic conditions 22,23. Kaneko et al., 378 Gene, 52-7 (2006); Wicki & Christofori, 96 Br. J. Cancer 96, 1-5 (2007). So far, no expression of PDP has been described on hematopoetic cells 23. Wicki & Christofori, 2007. This is the first work showing that PDP is expressed on some T cells and more specifically on differentiating TH17 cells (FIG. 10).

Figure 11:
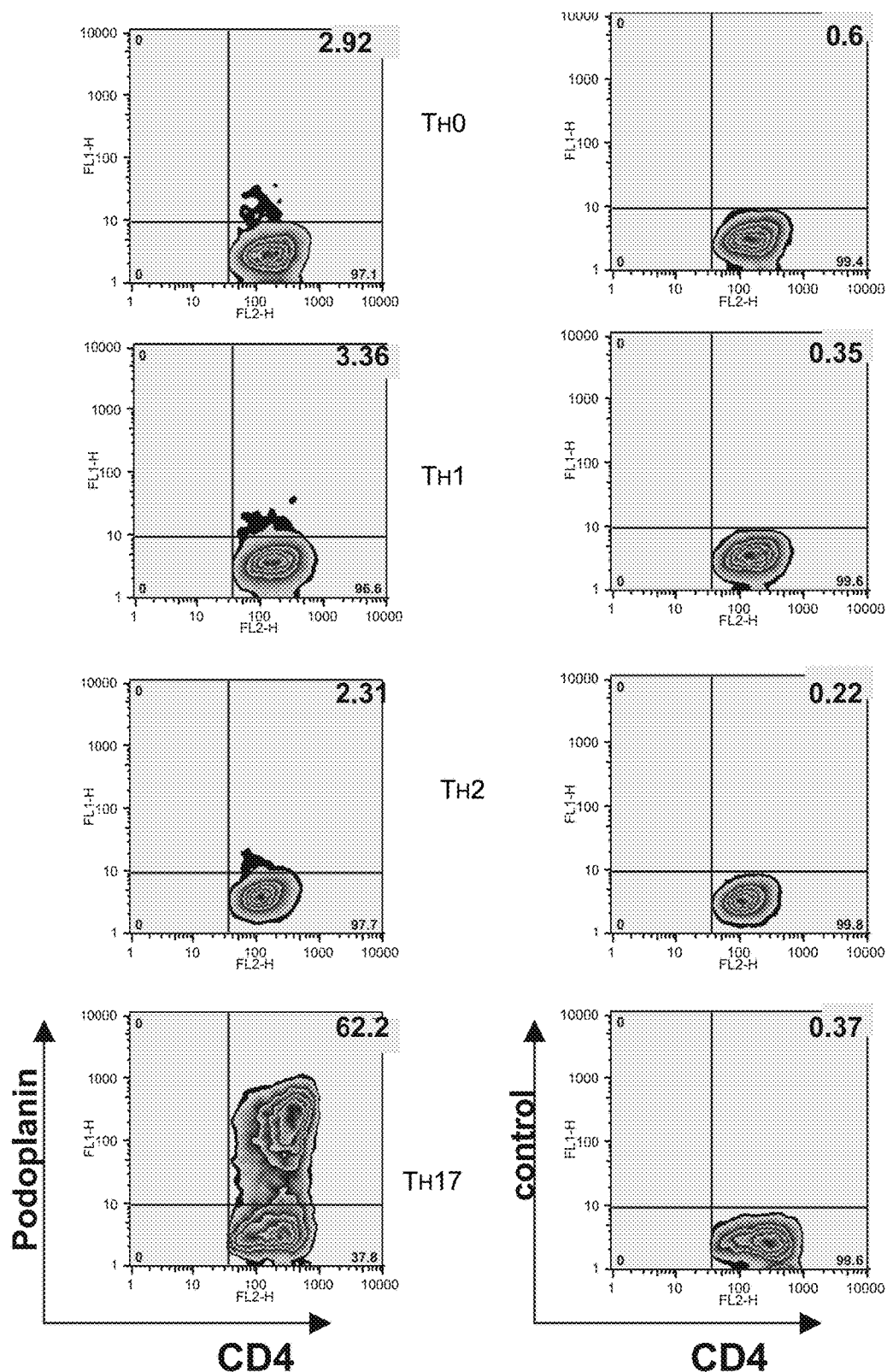
FIG. 11 shows the surface expression of podoplanin on different TH cell subsets.

Importantly, podoplanin constitutes a TH17 specific marker because its expression was not observed in TH1 or TH2 cells (FIG. 11). Therefore, it provides a specific marker to isolate and distinguish TH17 cells with minimal manipulation of T cells.

Figure 12:
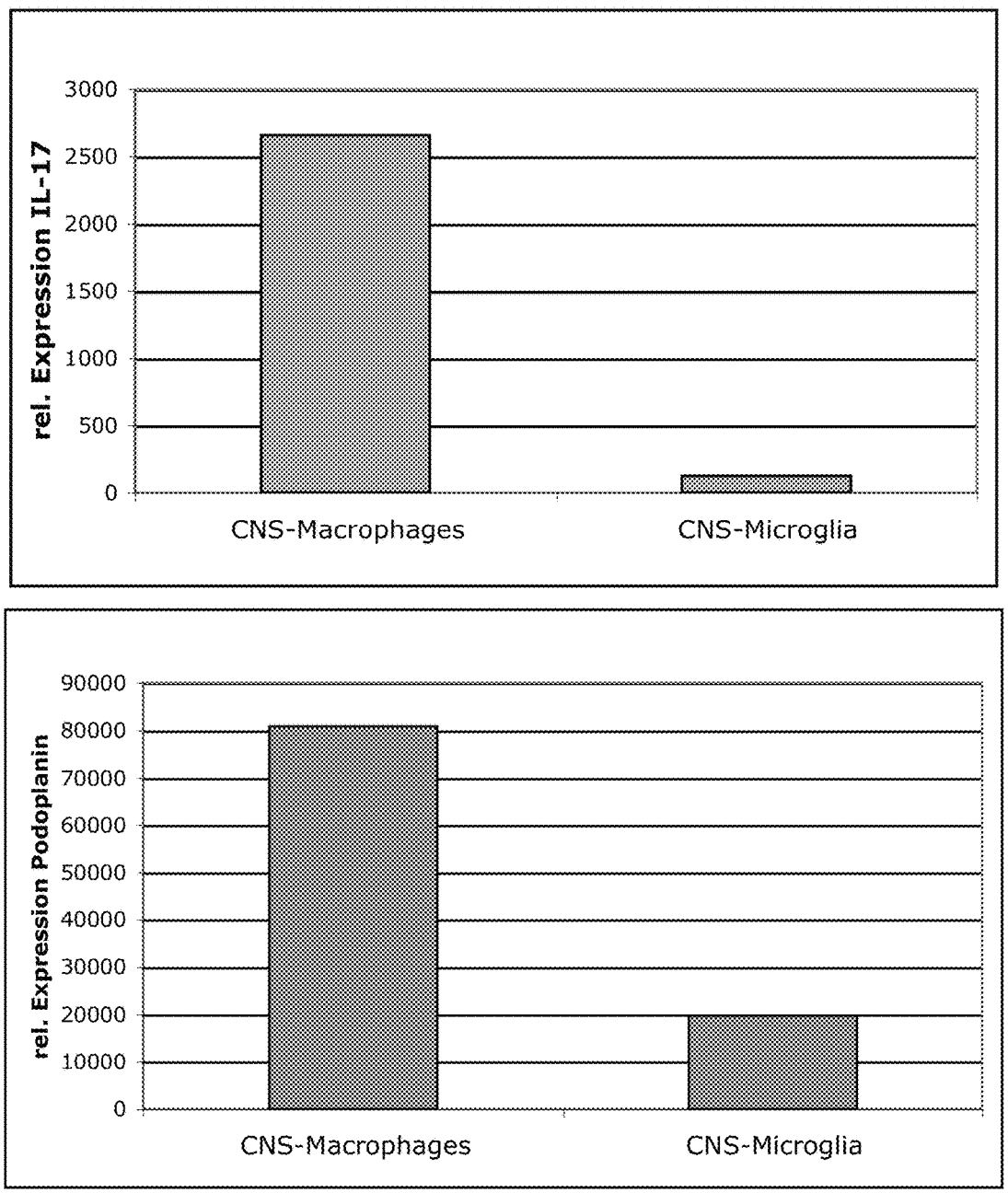
FIG. 12 demonstrates IL-17 and podoplanin expression on macrophages and microglia from the CNS during the course of EAE. C57BL/6 mice were immunized with MOG35-55 and pertussis toxin. When mice were paralyzed, at the peak of the disease, the CNS was collected and single cell suspensions were prepared. Macrophages (CD11b$^+$, CD45RB$^{hi}$) and microglial cells (CD11b$^+$, CD45RB$^{low}$) were sorted by flow cytometry. mRNA from these two populations was prepared and the expression of IL-17 and podoplanin determined by real time PCR using specific primers and probes.

In addition to TH17 cells, macrophages (CD11b+ cells) from the central nervous system (CNS) of mice with EAE were able to produce IL-17 (FIG. 12). Analysis of the expression of podoplanin on this population revealed that it expressed podoplanin as well. In contrast, microglial cells, did not express significant levels of either IL-17 or podoplanin. Therefore, it appears that podoplanin expression mimics IL-17 expression in both TH17 cells and macrophages, indicating that podoplanin expression can allow the tracking of subsets of pathogenic TH cells (TH17 cells) and also subsets of IL-17-producing pathogenic macrophages.

Example 4. BLT1 Modulates TH17 Function

Leukotriene B4 (LTB4), a degradation product of the arachidonic acid and a potent lipid inflammatory mediator generated rapidly at the site of inflammation, is derived from membrane phospholipids by the sequential actions of cytosolic phospholipase A2 (PLA2), 5-lipoxygenase (5-LO), and LTA4 hydrolase. Jala & Haribabu, 25 Trends Immunol 315-22 (2004). LTB4 is a potent chemoattractant that triggers the adherence and aggregation of leukocytes to the endothelium and recruits granulocytes and macrophages to the inflammation site. Recent studies have shown that LTB4 may also function as a chemoattractant for T cells. Goodarzi et al., 4 Nat. Immunol. 965-73 (2003); Tager et al., 4 Nature Immunol. 982-90 (2003); Tager & Luster, 69 Prostaglandins, Luekot. Essential Fatty Acids 123-34 (2003); Medoff et al., 202 J. Exp. Med. 97-110 (2005); Miyahara et al., 174 J. Immunol. 4979-85 (2005); Miyahara et al., 172 Am. J. Critical Care Med. 161-70 (2005).

Figure 3:
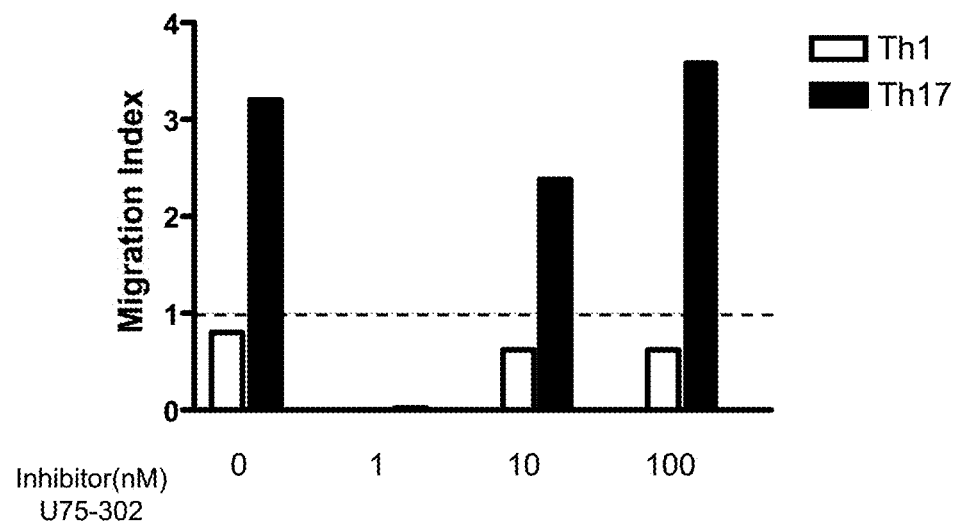
FIG. 3 presents data demonstrating that LTB4 induces the selective chemotaxis of TH17 cells. TH17 or TH1 cells alone or together with different concentrations of LTB4 inhibitor, U75-302, were added to the upper wells of chemotaxis chambers with 10$^{-8}$M of LTB4 in the lower wells. Cells were kept at 37° C. in 10% $CO_2$ for 2 hr. Cells from the lower chamber were then stained with anti-CD4 antibody and stimulated for 4 hr with PMA/ionomycin in the presence of Golgi Stop. Cells were permeabilized and stained intracellularly for IL-17 or IFN-γ. The chemotactic index was calculated by dividing the number of CD4$^+$ IL-17$^+$ (for TH17 cells) or CD4$^+$ IFN-γ+ (for TH1 cells) migrated cells in LTB4-containing wells by the number of CD4$^+$ IL-17$^+$ (for TH17 cells) or CD4$^+$ IFN-γ+ (for Th1 cells) cells that migrated spontaneously to media alone.

Because LTB4 is involved in the recruitment of different cell types at the site of inflammation, whether the expression of LTB4 could induce the selective migration of TH17 cells was investigated by manipulating its receptor, BLT1. Indeed, LTB4 induced the selective migration of newly differentiated TH17 cells but not TH1 cells (FIG. 3).

More specifically, two G-protein-coupled seven-membrane-domain receptors for LTB4 have been identified and characterized. Tager & Luster, 2003. BLT1 (also called LTBR1) is a high affinity receptor specific for LTB4 and is expressed primarily in leukocytes, whereas BLT2 (LTBR2) is a low affinity receptor expressed more ubiquitously. Id. U-75302, 6-(6-(3R-hydroxy-1E,5Z-undecadien-1-yl)-2-pyridinyl)-1,5S-hexandiol, is a synthetic, specifically binds BLT1. Richards et al., 140 Ann. Rev. Respir. Dis. 1712-16 (1989). U-75302 is available commercially from, e.g., Cayman Chemical (Ann Arbor, Mich.)). Using U75302 as an antagonist of LTB4, it was shown that LTB4 induced a selective migration of Th17 cells, which could be blocked in a dose dependant manner by the addition of different doses of the LTB4 antagonist U-75302 (FIG. 3).

Figure 4:
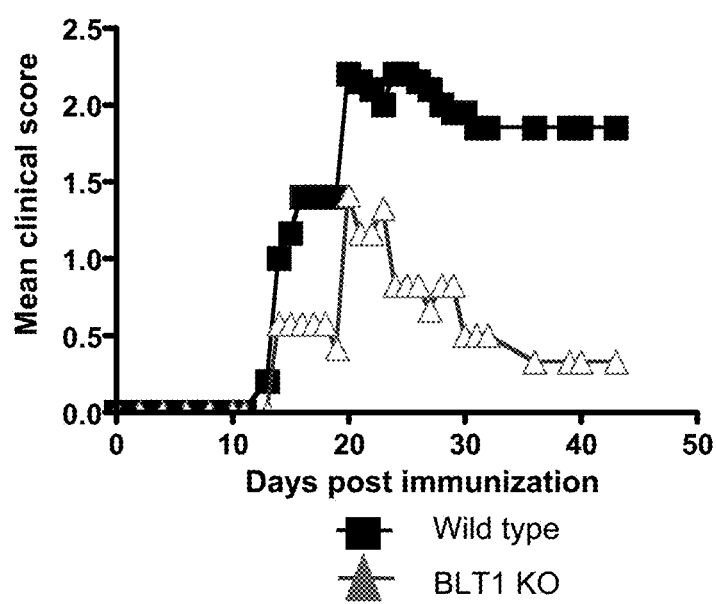
FIG. 4 shows the clinical course of autoimmune encephalomyelitis (EAE) in wild type and BLT1 knock-out (BLT1 KO) mice immunized with myelin antigen MOG35-55 for the development of EAE. BLT1 KO and C57BL/6 wild type mice were immunized with MOG35-55 and pertussis toxin. Mice were scored according to an EAE scale from 0 to 5. The graph represents the clinical course of EAE over time.

Additionally, the expression of BLT1 on TH17 cells also modulates the function of Th17 cells in vivo, as shown herein. This was determined by testing the effect of BLT1 ablation on the development of experimental autoimmune encephalomyelitis (EAE), an animal model of multiple sclerosis, in which TH17 cells have been shown to play an important pathogenic role. To do so, BLT1 knock-out (BLT1 KO) and wild type mice were immunized with myelin oligodendrocyte glycoprotein immunodominant peptide sequence MOG35-55 (encephalitogenic peptide) and injected with pertussis toxin. Mice were maintained according to IACUC protocols. The MOG35-55/pertussis toxin protocol resulted in the development of severe paralysis in wild type animals (FIG. 4). In contrast, BLT1 KO mice immunized with the myelin antigen MOGG35-55 developed less severe diseases compared to the wild type mice, indicating that the lack of BLT1 decreased the development of EAE. In addition, BLT1 (LTB4R1) deficient mice were more resistant to the development of EAE than their wild type littermates. Together, these data indicate that, in addition to tracking TH17 cells selectively, BLT1 expression modulates the functions of TH17 cells in vivo.

Example 5. Podoplanin Modulates TH17 Function

Figure 5:
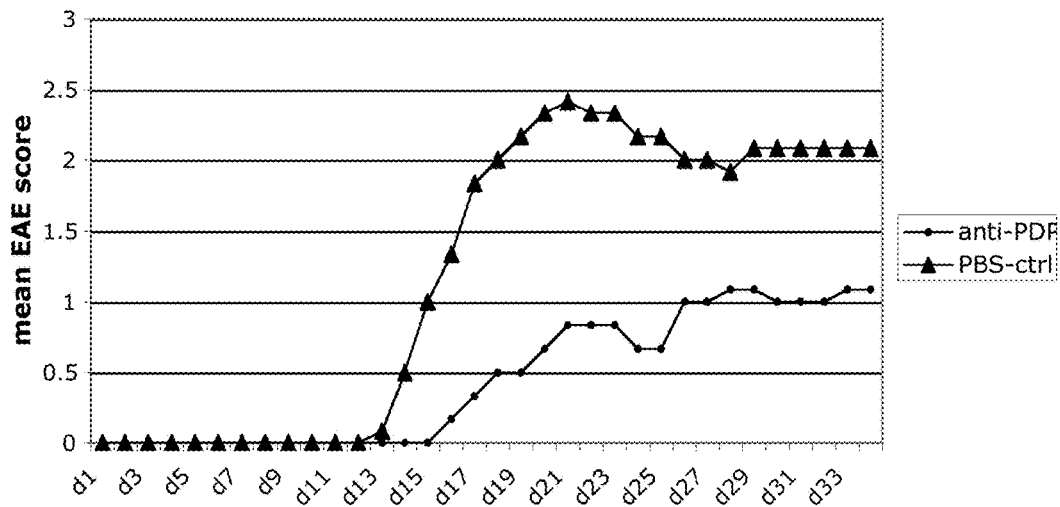
FIG. 5 shows an EAE course in C57BL/6 mice treated with anti-podoplanin antibody or control PBS. C57BL/6 mice were immunized with MOG35-55 plus pertussis toxin and injected with PBS or 100 μg of anti-podoplanin antibody on day 0, 2, 4, 6, 8 post-immunization. The graph represents the mean EAE clinical score for each group (n=6 mice in each group) over time.

Podoplanin was identified as a marker for TH17 cells, and its role in the progression of the animal model of multiple sclerosis, EAE, explored herein. An anti-podoplanin-specific antibody (Fan et al., 176 J. Exp. Med. 1477-82 (1992)), was injected in vivo into mice undergoing EAE. Although mice that received a control antibody developed severe disease and were paralyzed, the mice that received the anti-podoplanin specific antibody did not develop as severe disease, indicating that the anti-podoplanin antibody inhibited the progression of autoimmune disease. Therefore, these data indicate that injection of anti-podoplanin antibody can be used to block the pathogenic activity of TH17 cells and possibly IL-17-producing macrophages and therefore limit the progression of autoimmune diseases, as exemplified here using the animal model of multiple sclerosis, EAE. See FIG. 5.

Podoplanin has previously been shown to play an important role in the migration and invasiveness of tumor cells. Wicki & Christophori, 96 Br. J. Cancer, 1-5 (2007). Podoplanin was specifically expressed in Th17 cells and IL-17-producing macrophages. Furthermore, the injection of an anti-podoplanin antibody decreased the severity of EAE. Together, these data indicate that podoplanin can modulate the migration of pathogenic TH17 cells and possibly IL-17-producing macrophages. Determining how podoplanin is involved in the migration of TH17 cells is highly relevant to the treatment of autoimmunity, as the neutralization of podoplanin in an autoimmune setting could prevent further migration of Th17 cells in the CNS during MS attacks and improve relapsing remitting disease.

The invention claimed is:

1. A method for modulating the activity of a TH17 cell or TH17 cell population, comprising contacting said cell or population with an amount of TH17 activity modulator sufficient to modulate the activity of a TH17 cell or TH17 cell population, wherein said modulator comprises a podoplanin antagonist.

* * * * *